(12) United States Patent
Salasidis

(10) Patent No.: US 6,516,749 B1
(45) Date of Patent: Feb. 11, 2003

(54) APPARATUS FOR THE DELIVERY TO AN ANIMAL OF A BENEFICIAL AGENT

(75) Inventor: Robert Salasidis, Laval (CA)

(73) Assignee: Salasoft, Inc., Laval (CA)

( * ) Notice: Subject to any disclaimer, the term of this patent is extended or adjusted under 35 U.S.C. 154(b) by 0 days.

(21) Appl. No.: 09/335,591

(22) Filed: Jun. 18, 1999

(51) Int. Cl.⁷ ............................................... A01K 1/03
(52) U.S. Cl. .............................. 119/421 RPS; 604/65; 120/897
(58) Field of Search ................ 604/19, 21, 65, 604/66, 67; 607/19; 128/897–899; 119/53, 53.5, 54, 55, 57, 75, 76, 701, 174, 421, 454, 712

(56) References Cited

U.S. PATENT DOCUMENTS

| | | | |
|---|---|---|---|
| 4,146,029 A | 3/1979 | Ellinwood, Jr. | 128/260 |
| 4,627,839 A | 12/1986 | Young | 604/121 |
| 4,828,551 A | 5/1989 | Gertler et al. | 604/208 |
| 4,834,704 A | 5/1989 | Reinicke | 604/51 |
| 5,009,641 A | 4/1991 | Gorton | 604/131 |
| 5,069,668 A | 12/1991 | Boydman | 604/121 |
| 5,213,568 A * | 5/1993 | Lattin et al. | 604/20 |
| 5,232,448 A | 8/1993 | Zdeb | 604/153 |
| 5,466,227 A | 11/1995 | Kessenich | 604/246 |
| 5,531,773 A | 7/1996 | Lines | 607/46 |
| 5,560,317 A | 10/1996 | Bunyan et al. | 119/174 |
| 5,575,242 A | 11/1996 | Davis et al. | 119/721 |
| 5,593,431 A * | 1/1997 | Sheldon | 607/19 |
| 5,662,612 A | 9/1997 | Niehoff | 604/155 |
| 5,681,286 A | 10/1997 | Niehoff | 604/154 |
| 5,717,202 A | 2/1998 | Matsuda | 250/221 |
| 5,782,799 A | 7/1998 | Jacobsen et al. | 604/49 |
| 5,807,337 A | 9/1998 | Yamada et al. | 604/143 |
| 5,810,778 A | 9/1998 | Hjertman | 604/143 |
| 5,816,256 A | 10/1998 | Kissinger et al. | 128/897 |
| 5,832,878 A * | 11/1998 | Bonsall et al. | 119/769 |
| 6,062,224 A * | 5/2000 | Kissinger et al. | 128/897 |
| 6,086,582 A * | 7/2000 | Altman et al. | 606/41 |
| 6,168,569 B1 * | 1/2001 | McEwen et al. | 600/557 |
| 6,418,876 B1 * | 7/2001 | Hall et al. | 119/14.08 |
| 6,279,511 B1 * | 8/2001 | Loughnane | 119/769 |

* cited by examiner

Primary Examiner—Brian L. Casler
Assistant Examiner—Jennifer Maynard
(74) Attorney, Agent, or Firm—Ware, Fressola, Van Der Sluys & Adolphson

(57) ABSTRACT

An apparatus for the automatic delivery to an animal of a beneficial agent such as analgesia by infusion with the pain of the animal being taken into account when determining the rate of dispensing the agent. As the pain experienced by an animal and therefore its distress is manifested in increased agitation, the apparatus includes elements for the measurement of the frequency and amplitude of an animal's movement and the generation of a trigger signal when the either the frequency or the amplitude exceeds a predetermined threshold. The trigger can be used to generate a visual or audible alarm. The apparatus also preferably includes a dispensing means for delivering doses of beneficial agent to the animal in response to the trigger signal. The apparatus serves primarily to reduce the post-operative distress experienced by an animal by providing for timely administration of analgesic compounds. The apparatus also aids the animal care-giver by reducing the amount of time spent assessing the animal and administering beneficial compounds.

22 Claims, 3 Drawing Sheets

APPARATUS FOR THE DELIVERY TO AN ANIMAL OF A BENEFICIAL AGENT

FIELD OF THE INVENTION

The present invention relates to an apparatus for the delivery of a beneficial agent to an animal.

DESCRIPTION OF THE PRIOR ART

The automated dispensing of liquid medicine, such as analgesia, by infusion to relieve postoperative pain is increasingly being effected by using patient controlled or programmable infusion pump units. Typically, a programmable infusion pump unit includes an electronic infusion unit which can be readily activated by a patient. The patient is free to increase the dosage of medication in response to the pain experienced by repeatedly depressing an actuator. As the medication administered by such infusion pump units is often a narcotic analgesic, the unit is also equipped to limit the maximum dosage thus avoiding possible negative effects given the onset of an overdose.

The use of patient controlled and programmable infusion pumps has gained widespread acceptance based on a combination of their reliability in the timely administration of medication and the effect of relieving health care workers of the routine task of administering dosages of medication.

Animals undergoing surgery in a research or veterinary environment also invariably experience pain. In such an environment, ethics personnel closely supervise postoperative pain management in order to minimise any pain and suffering an animal may have. The current standard of care requires the animal to be assessed post-operatively by an animal-care giver, and to be medicated appropriately when there is a subjective impression of the presence of pain.

As animals cannot communicate verbally or cognitively activate an actuator in response to increased pain, one of the chief modalities used to make the assessment of pain is motion and agitation. The more extreme and rapid the motion, the more intense the pain which is being experienced by the animal. While this provides indicia to an animal care-giver of when to deliver appropriate analgesic medication, it often means that the animal is medicated only after the pain has reached intolerable levels. In addition, there is invariably a delay between animal experiencing the pain, the physical manifestation of the animal's distress, and the interpretation of the manifestation by the animal care-giver, who may have a number of animals in her care or may not have the animal under her surveillance at all times.

It is therefore desirable to provide an apparatus which can automatically measure the level of pain being experienced by an animal by interpreting the characteristics of the animal's motion. In addition, the level of pain can be used to provide for the infusion of an analgesic agent as an appropriate response with a dispensing apparatus operatively connected to the apparatus for measuring the level of pain; such an apparatus would aid the animal care-giver in the timely delivery of an analgesic agent thus reducing the animal's distress and freeing the animal care-giver to undertake other tasks.

SUMMARY OF THE INVENTION

It is an object of the present invention to provide an apparatus for the indication of pain felt by an animal. In accordance with the invention, this object is achieved with an apparatus comprising:

(a) at least one motion sensor for sensing motion of the animal, each of said motion sensors having an output; and
(b) a control unit operatively connected to the output of each motion sensor, the control unit being capable of generating a trigger signal when the output of the motion sensor exceeds a predetermined level, said trigger signal being indicative of the level of pain experienced by the animal.

The trigger signal can be used to trigger a visual or audible alarm, thereby calling an animal care-giver's attention to the animal in order to provide an adequate response.

Alternatively, the apparatus according to the invention can also further include a dispensing means operatively connected to the trigger signal of the control unit, the dispensing means causing a beneficial agent to be discharged from a storage chamber into the animal upon reception of the trigger signal. Consequently, the administration of medication can be automated in response to the output of the motion sensor, representative of the movement and agitation of the animal. In a preferred embodiment, the dispensing means is similar to a PCA as used for humans.

BRIEF DESCRIPTION OF THE DRAWINGS

The present invention and its advantages will be more easily understood after reading the following non-restrictive description of preferred embodiments thereof, made with reference to the following drawings in which.

DESCRIPTION OF A PREFERRED EMBODIMENT OF THE INVENTION

The invention is an apparatus for automatically measuring the level of pain experienced by an animal. The apparatus comprises at least one motion sensor for sensing motion of the animal, each of the motion sensors having an output; and a control unit 6 operatively connected to the output of each motion sensor, the control unit 6 being capable of generating a trigger signal when the output of the motion sensor exceeds a predetermined level.

In a first preferred embodiment of the invention, the motion sensor is inserted into a typical metabolic cage and consists of a motion platform 12 on which the animal 16 rests. The metabolic cage is of a size which limits the movement of the animal such that it may stand up or lie down, but may not turn around. This type of cage is sometimes required when multiple monitoring devices are present in the animal, which it could bite or scratch/rub off if allowed to roam free in a cage. As mentioned previously, the motion platform 12 is placed in the metabolic cage. The motion platform 12 is preferably made from aluminum with a grated surface, and is preferably coated with an epoxy-type finish to reduce the incidence of injury or blistering to the animal's legs. The grated surface allows the animal to defecate or urinate through the motion platform 12 without soiling itself. The motion platform 12 rests on four legs 13 that flex when weight is placed on them.

Figure 1:
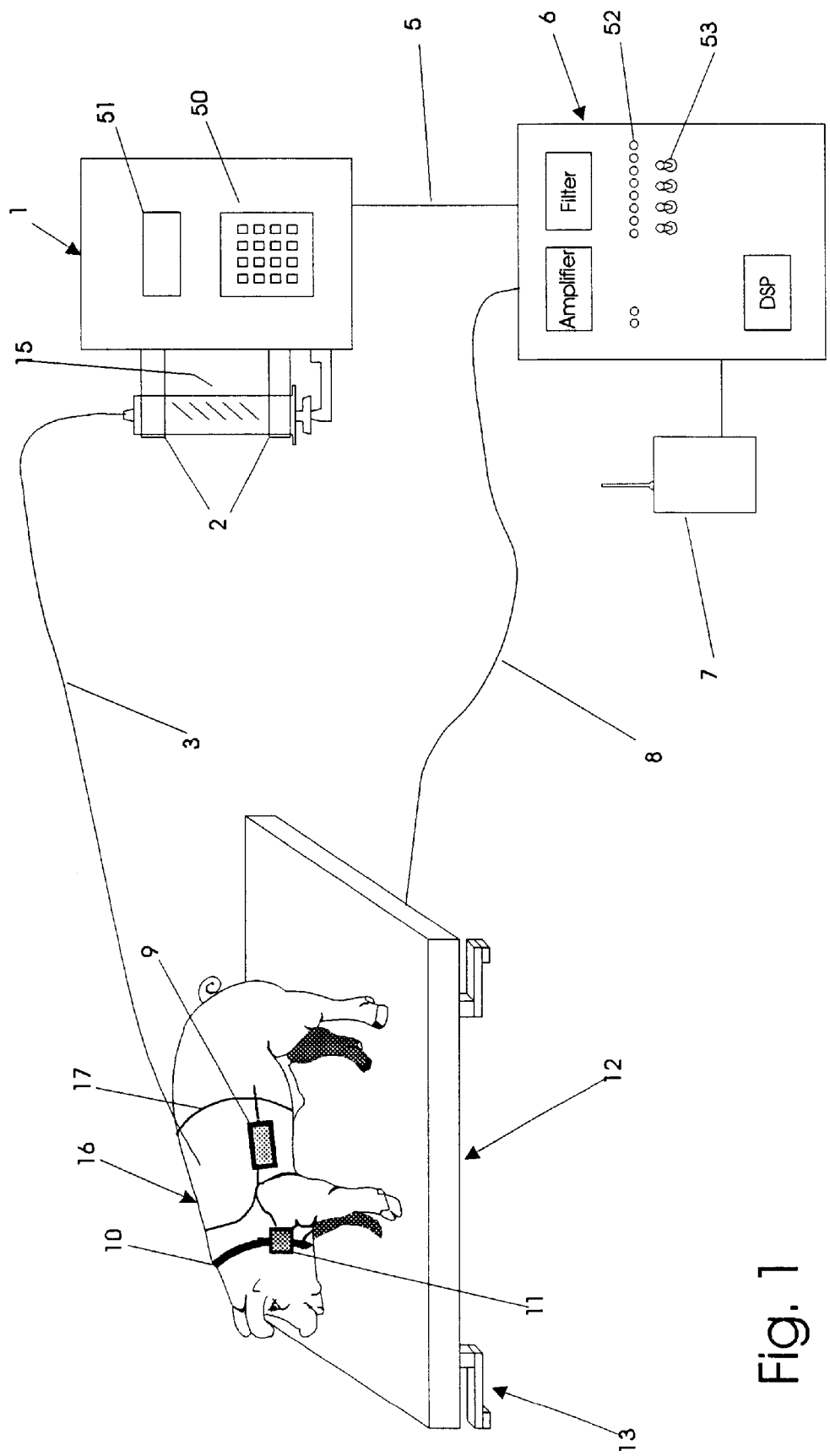
FIG. 1 is a block diagram of an apparatus to deliver a beneficial agent to an animal according to a preferred embodiment of the invention.
Figure 2:
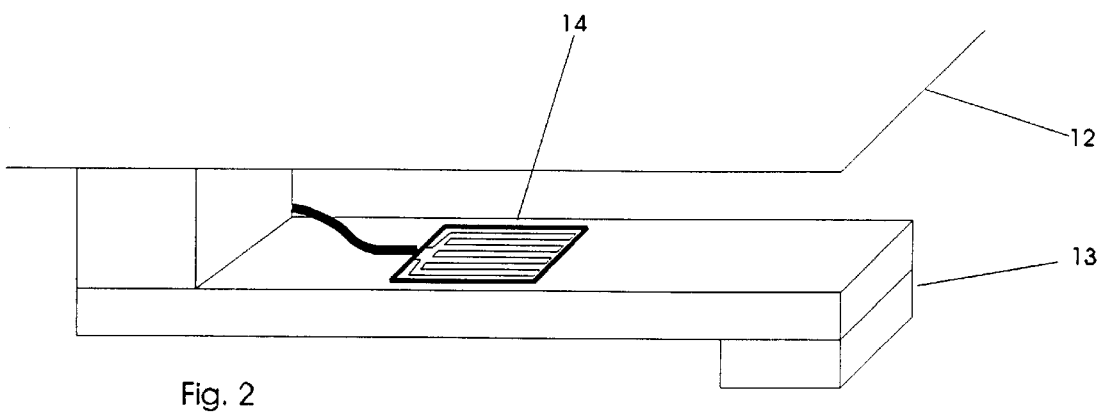
FIG. 2 is a detailed perspective view of a platform leg with strain gauge transducer attached.

Referring to FIG. 2, a detailed perspective view of a platform leg 13 with a strain gauge transducer 14 attached is shown. As the leg flexes, the strain gauge transducer 14 measures the extent of flexion, which is representative of the change of weight present on the leg. The four strain gauge transducers 14 attached to the four legs 13 of the motion platform are mounted in a Wheatstone bridge configuration (not shown) to provide the output 8 of the motion platform 12. Referring back to FIG. 1 the output 8 of the motion platform 12 is transferred to the control unit 6 via the motion platform output 8.

Accordingly, the motion platform 12 is limited by its requirements of a metabolic cage for its use. This severely limits the ability of the animal to move, and is not desirable when the animal would otherwise have been allowed to roam free within a larger cage.

Figure 3:
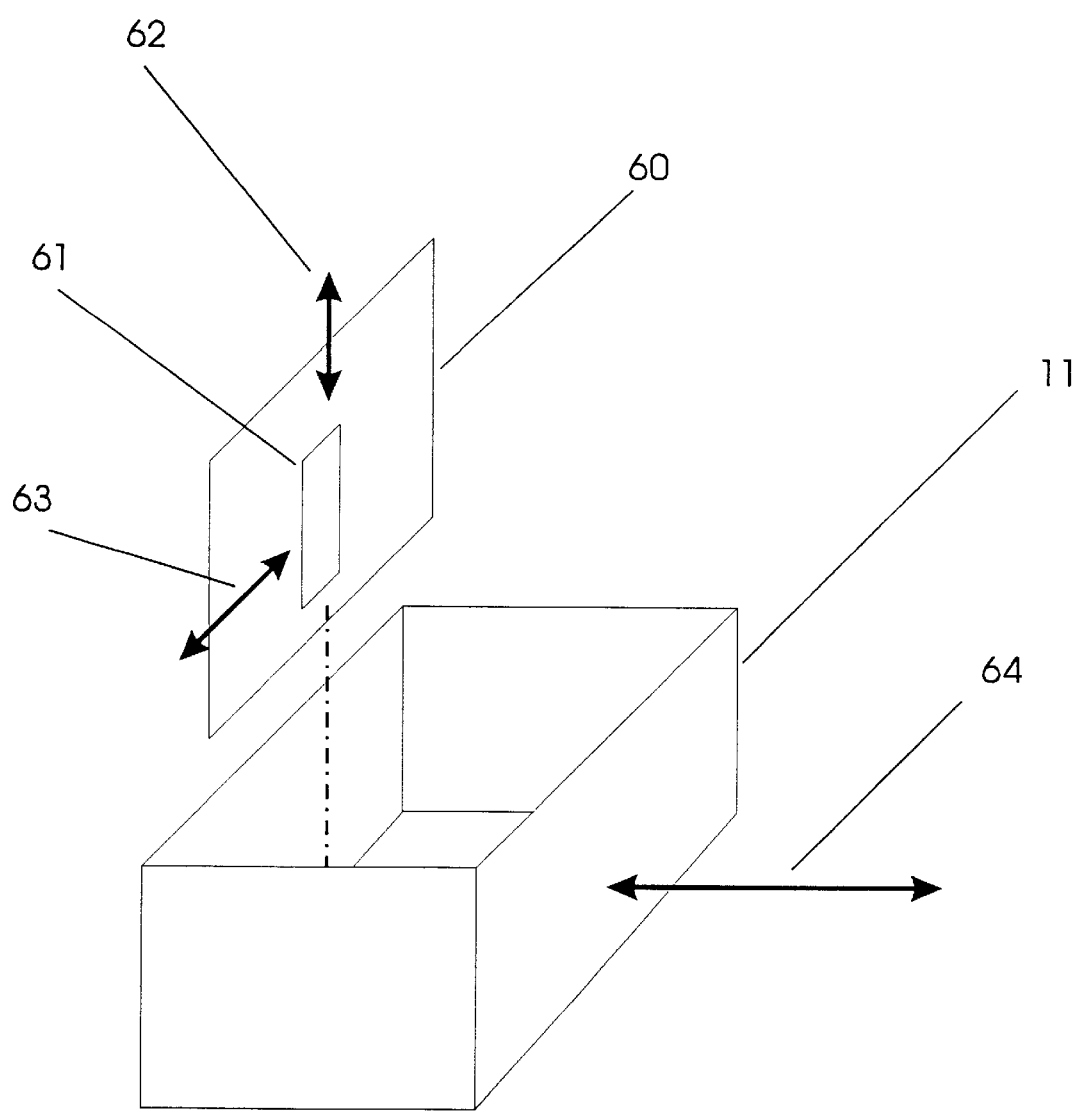
FIG. 3 is a schematic representation of an accelerometer for use in the apparatus according to the invention.

In a second preferred embodiment of the invention, the motion sensor is an accelerometer 11 attached snugly to the neck of the animal by means of a collar 10. The accelerometer 11 provides a low voltage output that varies directly with the motion of the animal. The accelerometer 11 is similar to those used in automobiles to sense sudden deceleration and deploy an airbag. The accelerometer 11 is an electronic circuit that senses acceleration and converts this to an electronic signal which can be read by the control unit 6. The accelerometer 11 senses acceleration on at least two axes, i.e. vertically when the animal moves up and down and side to side relative to the length of the animal. These types of movement are typical of those an animal might make when in distress. However, as long as both axes are at an angle with respect to the length of the animal, it will be sufficient for the invention. Preferably, as shown in FIG. 3, the accelerometer 11 is an X/Y accelerometer which senses acceleration along axes 62 and 63, which are preferably orthogonal to axis 64 (length of the animal).

The output of the accelerometer 11 is relayed to the control unit 6 via either a wire or an RF transmitter 9 and RF receiver 7 pair. If a wire is used, a swivel is required that attaches multiple wires and intravenous lines between a stationary platform and the animal. This swivel allows the animal to rotate infinitely without kinking the intravenous lines or tangling the wires coming off the motion sensor.

A swivel allows a simple connection between the ACA computer and the X/Y accelerometer but is expensive (wire+ intravenous swivels are much more expensive than intravenous swivels alone). In addition the swivel length may be short, minimizing the size of the area in a cage which the animal can be allowed to roam in. An RF transmitter receiver pair 9; 7 allows the accelerometer 11 to be attached to it so as to send out the acceleration signals by telemetry to a receiver that can be several hundred or more feet away. A lithium-ion battery that is selected for its lightweight and energy storage powers the transmitter 9. Under usual use, the transmitter 9 can send data up to 7 days continuously, without a recharge. In its current design, it weighs about 250 gm, but this can be decreased by at least half if shorter transmit times between recharges are acceptable. The size of the transmitter 7 is about 10×4.2×2.6 cms, it has a connector on one end for the X/Y accelerometer 11, and an antenna on the other end. The transmitter 9 contains a microcontroller that allows the coding of the accelerometer data in a digital format with embedded error correction and detection codes to allow error free transmission of data to the receiver. The X/Y accelerometer 11 on the neck collar is connected by a short cable to the transmitter which is tucked in a pocket on the animal's jacket 17 (jackets are used post-operatively to protect intravenous lines and incisions from scratching or biting by the animal). The size and weight of the jacket 17 used determine the size of the animal that can be monitored.

The X/Y accelerometer 11 when used without an RF transmitter 9, is small enough to be mounted on an animal the size of a cat. Larger animals can easily be monitored by telemetry using the transmitter 9.

The receiver 7 is plugged into the control unit 6, and receives the signal from the transmitter 9. It too contains a microcontroller, converting the digital signal back to the format originally transmitted by the accelerometer 9. It performs all the error detection required so as not to pass on invalid data to the control unit 6. Both devices have a frequency display that allows the user to select a frequency channel to use to communicate, therefore allowing more than one device to be used at the same time (as might be present in a busy environment where multiple post-operative animals are cared for simultaneously). The receiver 7 also has a display that shows the receiving signal and signal strength indicator (in case noise is present on that channel that makes communication difficult). A low battery warning is also present on the receiver (the transmitter sends a low battery signal when battery life is low).

Although two types of motion sensors are described herein, it should be understood that any type of sensor for sensing motion of an animal can be used for the purpose of the invention and they can be used singly or in combination.

The control unit 6 acts as an interpreter of the output of the at least one motion sensor and includes amplifying means, filtering means, and signal processing means. The control unit 6 amplifies and filters the motion sensor signal to remove any DC component such that the resulting signal is representative only of the movement of the animal. Signal frequencies greater than those in the region of interest are also filtered in order to reduce over all noise and improve the signal to noise ratio.

The filtering of the signal also removes DC components of the signal which could be related to the weight of the animal, or inaccuracies in the amplifiers. The resulting signal is then sampled at a frequency at least twice as high as the 3dB cut off of the high pass filter to prevent aliasing. A fast Fourier transform is used to convert the resulting samples from the time to the frequency domain which are then analyzed in respect to both signal frequency and signal amplitude. If a given signal is of either an amplitude or a frequency which exceeds a predetermined level, the control unit generates a trigger signal. A delay circuitry prevents the trigger signal from being generated more than once over a period of time, typically 2 to 5 seconds, to minimize the trigger signals generated by a single movement.

The predetermined levels of amplitude and frequency are set by means of a number of control switches 53 located on the control unit. Indicators 52 located on the control unit 6 provide visual clues as the motion being sensed in order to aid in the setting the predetermined levels of amplitude and frequency. All this of course could be done through a keyboard and display, and the control unit could be embodied in a personal computer.

Preferably, the signal amplitude or frequency is also filtered to remove signals falling below a minimum frequency to remove components related to slow, walking-type motion.

Accordingly, the motion sensor continually sends a signal to the control unit 6. The control unit 6 performs the signal processing and will generate a trigger signal when the output of the motion sensor falls outside a predetermined range. The trigger signal can be applied to a visual or audible alarm, alerting the animal care-giver's attention to the animal being monitored. Then, an appropriate action can be taken, such as administering a beneficial agent.

Alternatively, the control unit can be operatively connected to a dispensing means.

The dispensing means 1 is operatively connected to control unit 6 and responsive to the trigger signal, the dispensing means 1 causing the beneficial agent to be discharged from a storage chamber 2 into the animal upon reception of the trigger signal.

The dispensing means 1 is very similar to a Patient Controlled Analgesia (PCA) pump as widely used for human patients. The dispensing means 1 is composed of a holder 2 for a storage chamber 15 (here, as will typically be the case, a syringe), a pump 4 and a keyboard 50 and display 51. The dispensing means 1 is a self contained unit preferably encased in its own waterproof housing. The dispensing means 1 has a power source (not shown). An intravenous line 3 delivers the beneficial agent from the storage chamber 15 to the animal 16.

The keyboard 50 and display 51 are used to program variables and parameters into the dispensing means 1 for delivery of the drug contained in the storage chamber 15. The variables that can be programmed include the units of the drug to be given (for example in grams, milligrams, micrograms, etc.), the size of the storage chamber used, the concentration of drug present in the storage chamber and the volume of the storage chamber. Parameters for delivery include the number of trigger signals from the control unit 6 via the control unit output 5 required to give a dose, the dosage to give, the minimum delay which has to expire before a subsequent dose may be given, and a background infusion rate. The keyboard 50 and display 51 may also be used to program the dispensing means 1 to give doses of beneficial agent at predetermined times during the day, therefore extending the area of application of the dispensing means 1 to include the delivery of, for example, antibiotics or immuno-suppression drugs. The beneficial agent is driven from the storage chamber 15 by the pump 4 and introduced into the animal by means of an intravenous/muscular line 3.

Although the present invention has been explained hereinabove by way of a preferred embodiment thereof, it should be pointed out that any modifications to this preferred embodiment within the scope of the appended claims is not deemed to alter of change the nature and scope of the present invention.

What is claimed is:

1. Apparatus for determining a level of pain experienced by an animal, the apparatus comprising:
   (a) at least one motion sensor for sensing motion of the animal, each of said motion sensors having an output, said motion sensor output being divided into a frequency and an amplitude component for separate analysis thereof by a control unit;
   (b) the control unit operatively connected to the output of each motion sensor, the control unit being capable of generating a trigger signal when the output of the motion sensor exceeds a predetermined level, said trigger signal being representative of the level of pain experienced by the animal;
      wherein said apparatus further includes a dispensing means operatively connected to the trigger signal of the control unit, the dispensing means causing a beneficial agent to be discharged from a storage chamber into the animal upon reception of the trigger signal.

2. The apparatus as defined claim 1 wherein the motion sensor consists of an accelerometer attached to the animal.

3. The apparatus as defined in claim 2 wherein the accelerometer senses acceleration on at least two axes.

4. The apparatus as defined in claim 3 wherein the motion sensor is divided into said frequency and amplitude components for separate analysis thereof by the control unit.

5. The apparatus as defined in claim 4 wherein the control unit periodically samples the motion sensor output and calculates a frequency spectrum of the periodic samples.

6. The apparatus as defined in claim 3 wherein the control unit compares the frequency or amplitude, the control unit generating the trigger signal where either the frequency or the amplitude of the motion sensor output exceeds the corresponding predetermined level spectrum of the periodic samples with the predetermined level.

7. The apparatus as defined in claim 1 wherein the dispensing means determines a rate of delivery of the beneficial agent, the rate of delivery being determined by the level of pain experienced by the animal and the type of beneficial agent, the level of pain being related to the number of trigger signals per unit time.

8. The apparatus as defined in claim 7 wherein the dispensing means is adapted to deliver the beneficial agent at no greater than the predetermined rate of delivery.

9. The apparatus as defined in claim 8 wherein the control unit periodically samples the motion sensor output and calculates a frequency spectrum of the periodic samples.

10. The apparatus as defined in claim 9 wherein the control unit compares the frequency spectrum of the periodic samples with the predetermined level, the predetermined level consisting of the amplitude component and the frequency component.

11. The apparatus as defined in claim 8 wherein the motion sensor consists of a metabolic cage for housing the animal and wherein the motion sensor consists of a motion platform placed in the metabolic cage, the metabolic cage being of dimensions which prevent the animal from turning around while allowing the animal to stand or lie down.

12. The apparatus as defined in claim 11 wherein the motion platform is mounted on a plurality of legs, each of the legs being provided with a strain gauge transducer which flexes when weight is placed on it, the transducer converting the flexing into a signal.

13. The apparatus as defined in claim 7 wherein the motion sensor consists of a metabolic cage for housing the animal and wherein the motion sensor consists of a motion platform placed in the metabolic cage, the metabolic cage being of dimensions which prevent the animal from turning around while allowing the animal to stand or lie down.

14. The apparatus as defined in claim 13 wherein the motion platform is mounted on a plurality of legs, each of the legs being provided with a strain gauge transducer which flexes when weight is placed on it, the transducer converting the flexing into a signal.

15. The apparatus as defined claim 7 wherein the motion sensor consists of an accelerometer attached to the animal.

16. The apparatus as defined in claim 15 wherein the accelerometer senses acceleration on at least two axes, at least one vertical axis and at least one horizontal axis, where the horizontal axis is perpendicular to the length of the animal.

17. The apparatus as defined claim 8 wherein the motion sensor consists of an accelerometer attached to the animal.

18. The apparatus as defined in claim 17 wherein the accelerometer senses acceleration on two axes, a vertical axis and a horizontal axis, where the horizontal axis is perpendicular to the length of the animal.

19. The apparatus as defined in claim 1 wherein the control unit periodically samples the motion sensor output and calculates a frequency spectrum of the periodic samples.

20. The apparatus as defined in claim 19 wherein the control unit compares the frequency or amplitude spectrum of the periodic samples with the predetermined level, the control unit generating the trigger signal when either the frequency or the amplitude of the motion sensor output exceeds the corresponding predetermined level.

21. Apparatus for determining a level of pain experienced by an animal, the apparatus comprising:

(a) at least one motion sensor for sensing motion of the animal, each of said motion sensors having an output;

(b) a control unit operatively connected to the output of each motion sensor, the control unit being capable of generating a trigger signal when the output of the motion sensor exceeds a predetermined level, said trigger signal being representative of the level of pain experienced by the animal;

wherein the motion sensor consists of a metabolic cage for housing the animal and wherein the motion sensor consists of a motion platform placed in the metabolic cage, the metabolic cage being of dimensions which prevent the animal from turning around while allowing the animal to stand or lie down; and wherein said apparatus further includes a dispensing means operatively connected to the trigger signal of the control unit, the dispensing means causing a beneficial agent to be discharged from a storage chamber into the animal upon reception of the trigger signal.

22. The apparatus as defined in claim 21 wherein the motion platform is mounted on a plurality of legs, each of the legs being provided with a strain gauge transducer which flexes when weight is placed on it, the transducer converting the flexing into a signal.

* * * * *